United States Patent [19]

Belly et al.

[11] Patent Number: 4,952,495

[45] Date of Patent: Aug. 28, 1990

[54] HYDROLYZABLE COMPOUNDS WHICH RELEASE ELECTRON TRANSFER AGENTS AND ANALYTICAL USE OF SAME

[75] Inventors: Robert T. Belly, Ithaca; Patricia M. Scensny, Rochester; Annie L. Wu, Penfield; Chung-yuan Chen, Rochester, all of N.Y.

[73] Assignee: Eastman Kodak Company, Rochester, N.Y.

[21] Appl. No.: 59,667

[22] Filed: Jun. 8, 1987

[51] Int. Cl.$^5$ .................... C12Q 1/34; C07D 241/46
[52] U.S. Cl. .......................... 435/18; 435/4; 435/7; 435/14; 435/19; 435/21; 435/22; 435/23; 435/24; 558/37; 558/194; 530/408; 530/409; 530/410; 536/4.1; 536/17.4; 544/31; 544/337; 544/347; 552/296; 552/298; 548/368
[58] Field of Search ............... 435/4, 7, 14, 18, 19, 435/21, 22, 23, 24, 29, 810; 530/408, 409, 410; 536/4.1, 17.4; 544/31, 337, 347; 558/37, 194; 552/296, 298; 548/368

[56] References Cited

U.S. PATENT DOCUMENTS

| | | | |
|---|---|---|---|
| 2,372,655 | 4/1945 | Bockmuhl et al. | 558/37 |
| 3,201,385 | 8/1965 | Jarrett . | |
| 3,504,054 | 3/1970 | Cierpka et al. | 558/194 |
| 4,144,306 | 3/1979 | Figueras . | |
| 4,160,645 | 7/1979 | Ullman . | |
| 4,271,265 | 6/1981 | Deneke et al. . | |
| 4,273,870 | 6/1981 | Mollering et al. . | |
| 4,446,231 | 5/1984 | Self . | |
| 4,576,760 | 3/1986 | Imada | 558/37 |
| 4,716,222 | 12/1987 | Wallenfels et al. | 536/18.1 |
| 4,746,607 | 5/1988 | Mura et al. | 435/29 |

FOREIGN PATENT DOCUMENTS

| | | |
|---|---|---|
| 0670378 | 9/1963 | Canada ........................ 558/194 |
| 0060123 | 9/1982 | European Pat. Off. . |
| 0122148 | 10/1984 | European Pat. Off. . |
| 3510482 | 3/1985 | Fed. Rep. of Germany . |
| 61-221107 | 10/1986 | Japan . |
| 86/03837 | 7/1986 | PCT Int'l Appl. . |

OTHER PUBLICATIONS

Shiseido-I, Abstract of Japanese Patent 300705, 10/1/86.
Shiseido-II, Abstract of German Patent 3510482, 8/28/86.
Duerckheimer et al., Index Chemicus, 17, #50297, 1965.

*Primary Examiner*—Sam Rosen
*Attorney, Agent, or Firm*—J. Lanny Tucker

[57] ABSTRACT

Hydrolyzable substrates comprise blocked moieties which, when cleaved from the substrate during hydrolysis, provide electron transfer agents. The released electron transfer agents can be recycled between a reductant and a reducible compound that upon reduction provides a detectable species. Alternatively, they can be recycled between an oxidant and an oxidizable compound that upon oxidation provides a detectable species. These substrates are useful in analytical compositions, elements and methods for the determination of hydrolytic analytes, such as hydrolytic enzymes or biological cells containing such enzymes.

14 Claims, No Drawings

HYDROLYZABLE COMPOUNDS WHICH RELEASE ELECTRON TRANSFER AGENTS AND ANALYTICAL USE OF SAME

FIELD OF THE INVENTION

This invention is useful in the field of clinical chemistry. It relates to hydrolyzable compounds and to analytical compositions and elements containing same. It also relates to a method for the determination of hydrolytic analytes using the hydrolyzable substrates.

BACKGROUND OF THE INVENTION

Chemical analysis of liquids, such as water, milk and biological fluids is often desirable or necessary for health maintenance and diagnosis and treatment of disease. Various compositions and elements to facilitate such analyses are known. Such materials generally comprise a reagent composition for determining the substance under analysis, identified herein as an analyte. The analyte can be living cells, such as yeast cells, white blood cells, bacteria or other living organisms, or a nonliving chemical substance such as an enzyme. The reagent composition, upon interaction with the analyte, provides a detectable change (for example, dye formation) which can be quantified in some manner.

The determination of specific hydrolytic enzymes in biological fluids can be useful for the diagnosis and treatment of diseases. It can also be useful for determining the presence of certain microorganisms because the metabolism of the microorganism is dependent upon the presence of certain hydrolytic enzymes.

A number of analytical procedures have been developed whereby a substrate for an enzyme of interest is hydrolyzed to release a detectable moiety. These procedures use both colorimetric and fluorometric dyes. Fluorometric assays are generally preferred because of generally greater sensitivity. E. P. Publication 122,148 describes an assay for microorganisms using certain coumarin derivatives as substrates which release dyes when the substrate is hydrolyzed. Other known assays utilize diazonium compounds to provide detectable moieties in response to hydrolytic analytes (see U.K. Patent Application 2,031,949).

A significant advance in the art is described in U.S. Ser. No. 824,766, filed Jan. 31, 1986, entitled REDUCIBLE COMPOUNDS AND ANALYTICAL COMPOSITIONS, ELEMENTS AND METHODS OF UTILIZING SAME. This application describes useful reducible compounds which, when reduced by a reductant (such as NADH) in a test sample, provide a detectable species, such as a chromogen or fluorogen. Many of the detectable species so released have high extinction coefficients, thus providing high sensitivity to low concentrations of analytes. It would be desirable to use such compounds in the detection of hydrolytic analytes, such as hydrolytic enzymes found in various organisms. However, hydrolytic enzymes and their substrates are not always reductants for such reducible compounds.

It has been found that the reduction of some reducible compounds can be undesirably slow. In such cases, an electron transfer agent can be used to facilitate compound reduction. However, even in these reactions, only one equivalent of detectable species is released for each equivalent of electron transfer agent used. Therefore, it would be desirable to have a more sensitive assay, that is, an assay wherein more than one equivalent of detectable species is released from only one equivalent of electron transfer agent.

SUMMARY OF THE INVENTION

The problems noted above have been overcome in this invention with the use of a reducible or oxidizable compound with a hydrolyzable compound represented by the formula:

BLOCK-ETA wherein BLOCK is a hydrolyzable group, and ETA is a group derived from an electron transfer agent that when released, provides an electron transfer agent in either its oxidized or reduced form, the BLOCK and ETA being connected through the redox active portion of the electron transfer agent. In preferred embodiments, the electron transfer agent is a phenazine, naphthazine, phenothiazine or phenazonium compound, or a substituted benzo- or naphthoquinone, as described herein.

This invention also provides an analytical composition comprising: (a) either a reducible compound or an oxidizable compound, and (b) the hydrolyzable compound described above.

Further, a dry analytical element of this invention which is useful for the determination of a hydrolytic analyte comprises an absorbent carrier material, and contains the hydrolyzable compound described above.

Further, a method for the determination of a hydrolytic analyte comprising the steps of:

A. under hydrolyzing conditions, contacting a sample of a liquid suspected of containing a hydrolytic analyte with the hydrolyzable compound described above, the contacting being carried out in the presence of either a reducible compound or an oxidizable compound which can be either reduced or oxidized, respectively, by the electron transfer agent to provide a detectable species, and B. determining the detectable species provided from either the reduction or oxidation of the reducible or oxidizable compound, respectively.

In a preferred embodiment, the method described above is carried out in the presence of either (1) a reducible compound that can be reduced by the released electron transfer agent to provide a detectable species, and a reductant that can then reduce the oxidized electron transfer agent, or (2) an oxidizable compound that can be oxidized by the released electron transfer agent to provide a detectable species, and an oxidant that can then oxidize the reduced electron transfer agent.

The present invention provides novel substrates which release electron transfer agents upon hydrolysis by hydrolytic analytes. These released electron transfer agents can be in either a reduced or oxidized form, and facilitate either the reduction of reducible compounds or the oxidation of oxidizable compounds to provide a detectable species. Thus, these substrates can be used in an assay for hydrolytic analytes to provide a more sensitive and rapid determination.

In one embodiment, a stoichiometric excess of a reductant, which is capable of reducing the oxidized electron transfer agent, is also present. This reductant will reduce the electron transfer agent at a much faster rate than the reducible compound. Alternatively, in another embodiment, a stoichiometric excess of an oxidant, which is capable of oxdizing the reduced electron transfer agent, is also present. This oxidant will oxidize the electron transfer agent at a much faster rate than the oxidizable compound. As a result, one equivalent of the released electron transfer agent can be recycled to produce more than one equivalent of detectable species, giving an amplified, highly sensitive assay.

The reaction of the reducible compound with the reductant, or the reaction of the oxidizable compound with the oxidant must be slow in the absence of the electron transfer agent. This can be accomplished in any of several ways, including electrochemically by adjusting redox potentials, or by adjusting the physical or chemical reaction conditions (for example, temperature, pH, concentration of reagents or immobilization of reactants within micelles).

DETAILED DESCRIPTION OF THE INVENTION

The present invention can be used to determine qualitatively or quantitatively a hydrolytic analyte (living or nonliving). As used in this application the term "hydrolytic analyte" refers to a substance (chemical substance, enzyme or organism) which is capable of hydrolyzing the substrate of this invention by cleaving the BLOCK group from the remainder of the molecule. This invention is particularly useful for determining hydrolytic enzymes, such as acylases, esterases, amidases, glycosidases, phosphatases, and microorganisms containing these enzymes, such as members of the Enterobacteriaceae or Neisseriaceae family, including those enzymes and microorganisms listed in PCT Patent Application 80/02433 (published Nov. 13, 1980). The substrate can be designed with the appropriate BLOCK group and linkage to determine a particular analyte.

The substrates of this invention can be used in analytical determinations of various aqueous liquids, for example, biological fluids, manufacturing processes, wastewater, food stuffs, etc. The determinations can be made via a single reaction or a sequence of reactions which brings about hydrolysis of the substrate and release of the electron transfer agent.

The present invention is particularly useful for the determination of hydrolytic enzymes, cells or microorganisms containing such enzymes which may be found in biological fluids, for example, urine, cerebral spinal fluid, blood, lymph fluids, tissue homogenate, mucous, saliva or stool secretions.

The substrates of this invention are represented by the formula:

BLOCK-ETA.

In this formula, BLOCK represents any suitable hydrolyzable group which can be cleaved from the remainder of the molecule by hydrolysis. In the context of this application, the BLOCK group blocks or inhibits the inherent electron transferring capability of the electron transfer agent (identified as ETA) by means of redox blocking. This means that BLOCK is connected to ETA through the redox active portion of the electron transfer agent molecule so that ETA is inactive when attached to BLOCK and active when released. The specific redox active portion of each electron transfer agent is well known to a skilled chemist. The blocking group can be chosen based on the analyte specificity desired. Representative blocking groups include, for example, —CO—R*, phosphono or thioxophosphono or a salt thereof, or a moiety derived from an amino acid, peptide or mono-, oligo- or polysaccharide.

R* can be hydrogen, substituted or unsubstituted alkyl (preferably of 1 to 20 carbon atoms, for example, methyl, ethyl, chloroethyl, isopropyl, benzyl or chlorobenzyl), substituted or unsubstituted alkenyl (preferably of 2 to 20 carbon atoms, for example, ethenyl, 2-propenyl or 4-hexenyl), substituted or unsubstituted aryl (preferably of 6 to 12 carbon atoms, for example, phenyl or methoxyphenyl), substituted or unsubstituted cycloalkyl (preferably of 5 to 12 carbon atoms, for example, cyclopentyl or cyclohexyl), or a substituted or unsubstituted heterocyclic group (preferably of 6 to 12 carbon, sulfur, nitrogen and oxygen atoms, for example, pyridyl or thienyl).

ETA represents any electron transfer agent that can be redox blocked as described above and eventually released. Many electron transfer agents are known in the art, but this invention is not limited to the use of compounds which are currently known. As used herein, an electron transfer agent is a compound which has a redox potential such that it is capable of both receiving and giving up one or more electrons in the presence of either reducible or oxidizable compounds.

ETA is connected to BLOCK through a single bond, or through a linking group which is part of the ETA moiety. Such linking groups include oxy, thio, or imino [—NR—, wherein R is hydrogen or substituted or unsubstituted alkyl of 1 to 10 carbon atoms, for example, methyl, chloromethyl, ethyl, propyl, isopropyl, decyl or benzyl, substituted or unsubstituted cyclohexyl (for example, cyclohexyl or 4-methylcyclohexyl), substituted or unsubstituted phenyl (phenyl, chlorophenyl or p-methoxyphenyl), sulfonyl (—$SO_2R'$ wherein R' is alkyl or phenyl as defined for R), or a substituted or unsubstituted heterocyclic group as defined above, for example, pyridyl or thienyl]. Preferably, ETA is connected to BLOCK through an oxy or imino group wherein R is hydrogen or lower substituted or unsubstituted alkyl of 1 to 3 carbon atoms.

Representative electron transfer agents from which ETA is derived include the phenazines, such as phenazine methosulfate and phenazine ethosulfate, the naphthazines, such as Roseinduline 2G, the phenothiazines, such as thionine, the phenazonium compounds, such as Cresyl blue (and others described by Furst et al, *Anal. Chim. Acta*, 140, pp. 1-18, 1982, Table 2), and substituted o- or p- benzo- and naphthoquinones, some of which are generally described in U.S. Ser. No. 699,374, filed Feb. 7, 1985 by Mura et al now U.S. Pat. No. 4,746,607 and U.S. Ser. No. 053,916, filed May 26, 1987 by Mura et al and entitled "Use of Substituted Ortho-Quinones as Electron Transfer Agents in Analytical Determinations". Particularly useful compounds in the practice of this invention include phenazine methosulfate, phenazine ethosulfate and the o- or p- benzo- and naphthoquinones noted above.

The details of preparing the substituted benzo- and naphthoquinones described herein can be obtained by consulting U.S. Ser. Nos. 699,374 and 053,916, noted above. In general, the compounds are those having the structure (I):

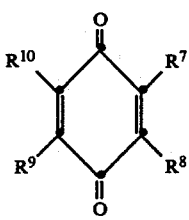

In this structure, $R^7$ and $R^8$ are independently hydrogen, hydroxy, halo (for example, fluoro, chloro, bromo or iodo), cyano, nitro, carboxy, carboxyalkyl wherein the alkyl has 1 to 10 carbon atoms (such as carboxymethyl or carboxyethyl), carboxamido (that is, —CONR'R" where R' and R" are independently hydrogen, alkyl or aryl as defined below), sulfonamido (that is, —SO$_2$NR'R" wherein R' and R" are as defined above), trihaloalkyl wherein the alkyl group has 1 to 10 carbon atoms (such as trichloromethyl, tribromomethyl or trifluoromethyl), sulfonyl (that is, —SO$_2$R''' wherein R''' is alkyl or aryl as defined below), carboxaldehyde, carbonylalkyl wherein the alkyl group has 1 to 10 carbon atoms (such as acetyl), substituted or unsubstituted alkyl or alkenyl (generally of 1 to 10 carbon atoms, for example, methyl, ethyl, chloromethyl, 2-propenyl, n-hexyl or decyl and preferably of 1 to 5 carbon atoms), substituted or unsubstituted alkoxy (defined similarly to alkyl), substituted or unsubstituted hydroxyalkyl (generally of 1 to 10 carbon atoms, for example, hydroxymethyl, hydroxyethyl, 2-hydroxypropyl or 2-hydroxyisopropyl wherein the alkyl portion can be further substituted and preferably of 1 to 5 carbon atoms), substituted or unsubstituted hydroxyalkoxy (defined similarly to hydroxyalkyl), substituted or unsubstituted acetoxyalkyl (generally of 1 to 10 carbon atoms in the alkyl portion of the molecule which can be defined as for alkyl above, for example, acetoxymethyl or acetoxyethyl and preferably of 1 to 5 carbon atoms), substituted or unsubstituted acetoxyalkoxy (generally of 1 to 10 carbon atoms in the alkoxy portion of the molecule and defined similarly to acetoxyalkyl above, and preferably of 1 to 5 carbon atoms), substituted or unsubstituted alkoxyalkyl or oxyalkylenealkoxy (each generally having 2 to 10 carbon atoms with the alkoxy and alkyl portions of the molecule defined as noted above, and alkylene having 1 to 5 carbon atoms), substituted or unsubstituted aryl (generally of 6 to 12 carbon atoms, for example, phenyl, naphthyl, xylyl, methylnaphthyl or p-methoxyphenyl), substituted or unsubstituted alkaryl (generally of 7 to 10 carbon atoms, with the alkyl and aryl portions of the molecule defined similarly to alkyl and aryl above, for example, benzyl, phenylethyl or p-methoxyphenylethyl), heterocyclic or alkylheterocyclic groups (generally of 5 to 12 carbon, nitrogen, oxygen or sulfur atoms in the ring, with one or more substituents if desired, for example, morpholino, piperidino or methylpiperidino).

Also, in structure I above, $R^9$ and $R^{10}$ are independently selected from the groups described for $R^7$ and $R^8$, or taken together, supply the carbon, nitrogen, oxygen or sulfur atoms to complete a 4- to 8-membered fused substituted or unsubstituted carbocyclic or heterocyclic ring attached to the quinone nucleus (for example, to complete a cyclopentane, dihydrofuran, or bicyclic ring, such as bicyclo[2 · 2 · 2]octane, benzo, or a bicyclo[2 · 2 · 1]heptane ring).

At least one of the substituents, $R^7$, $R^8$, $R^9$ and $R^{10}$, is not hydrogen, but is one of the groups defined above, or is taken with another substituent to form the defined fused ring.

Examples of some useful substituted benzo- and naphthoquinones are shown in U.S. Ser. Nos. 699,374 and 053,916, noted above.

The hydrolyzable substrates of this invention are prepared by the following general procedure: preparation or purchase of the electron transfer agent followed by its reaction with an appropriate blocking moiety. The blocking moiety may be purchased or prepared using standard chemistry. Before reaction with an electron transfer, the reactive groups on the blocking moiety are protected with protective groups so that reaction with the electron transfer agent occurs at one position only. Once reaction is accomplished, the protective groups are removed. Particular details regarding representative syntheses are described in Examples 1–3 below.

A hydrolytic analyte is assayed according to this invention by contacting a sample of fluid suspected of containing the analyte with both the hydrolytic substrate described above and either a reducible compound or an oxidizable compound. The substrate and reducible or oxidizable compound can be provided separately or together in an analytical composition.

In a preferred embodiment, a hydrolytic analyte is assayed by contacting a sample of fluid suspected of containing the analyte with the hydrolytic substrate, a reducible compound and excess reductant, or an oxidizable compound and excess oxidant. The substrate and the reducible or oxidizable composition can be provided separately or together as an analytical composition.

In the reduction embodiment, reducible compounds useful in the practice of this invention are broadly defined as organic compounds which provide a detectable signal in response to reduction by an electron transfer agent in its reduced form. Such a signal can be provided by the compound itself or a part thereof which is released in some fashion. Representative reducible compounds include tetrazolium salts, leuco dyes, 2,6-dichloroindophenol and others known to one skilled in the art.

One class of useful reducible compounds is the cobalt containing compounds described in commonly assigned and copending U.S. Ser. No. 890,050, filed Jul. 28, 1986 by Schmittou and entitled COBALT CONTAINING REAGENTS AND METHODS FOR THE DETERMINATION OF ANALYTES IN AQUEOUS FLUIDS.

Particularly useful reducible compounds are the reducible compounds described in U.S. Ser. No. 824,766, noted above. These compounds contain a shiftable detectable species which can be reduced at physiological pH (that is, 9 or less) to release the shiftable detectable species. The term "shiftable detectable species" is defined as: (1) a chromogen moiety, which has a first spectral absorption band while attached to the reducible compound and a second spectral absorption band when released, or a fluorogen moiety which has first spectral absorption and emission bands while attached and second spectral absorption and emission bands when released, (2) a chemically or biologically useful moiety which is inactive, blocked or otherwise inaccessible when attached to the reducible compound but active, unblocked or accessible when released, or (3) a chemically or biologically useful moiety which is active or accessible when attached to the reducible compound but inactive or otherwise inaccessible when released.

Thus, a shiftable detectable species is a moiety which has a first spectral absorption band while attached to the reducible compound before reduction and release, but which exhibits a second spectral absorption band during analytical measurement. The detectable species is chemically modified when attached to the reducible compound nucleus so that the spectral absorption band of the reducible compound is "shifted" from the band that the species has when released. Generally, but not necessarily, the band is relocated to substantially shorter wavelengths when the species is a part of the reducible compound. In all cases, the two bands do not overlap to a significant extent. The change from one spectral absorption band to another can be due to the mere release of the moiety from the reducible compound, or alternatively, it can be caused by such release coupled with either interaction of the released moiety with metal ions or a mordant, or coupled with a change in the assay environment (for example, a change in pH).

As noted above, shiftable detectable species can also be chemically or biologically useful moieties which, when attached to the reducible compound, are inactive or blocked or otherwise inaccessible, but when released at physiological pH become biologically or chemically active or accessible for further interaction. The released, active species can be detectable itself or is capable of one or more subsequent chemical, physical or biological reactions to provide a detectable species. The practice of this invention provides a means for releasing such moieties, for example, enzymes, enzyme substrates, enzyme inhibitors, cofactors, catalysts or reactants upon reduction of the reducible compound, preferably at physiological pH, for a variety of chemical or biological purposes.

Further, a shiftable detectable species can be a chemically or biologically useful moiety which, when attached to the reducible compound, is active, or otherwise accessible for one or more subsequent chemical, physical or biological reactions, but when released at physiological pH becomes inactive or otherwise inaccessible for such reactions.

The reducible compounds especially useful in this invention have the structure CAR$-$(R$^1$)$_n$ wherein CAR$-$ represents a substituted or unsubstituted aromatic or quinone nucleus, R$^1$ is a moiety comprising a shiftable detectable species defined below, and n is 1 or 2. Examples of such nuclei are presented below. Further, when R$^1$ is replaced by H, CAR$-$(H)$_n$ has a reduction potential (E$_{\frac{1}{2}}$) of either at least about $+100$ mV when measured in water, or of at least about $-650$ mV when measured in acetonitrile. This E$_{\frac{1}{2}}$ value facilitates the reduction and subsequent release of the shiftable detectable species from the compound. Such measurements are made according to standard electrochemical techniques using either differential pulse polarography or cyclic voltametry. Preferably, the E$_{\frac{1}{2}}$ is from about $+100$ mV to about $+400$ mV as measured in water, or from about $-650$ to about $-300$ mV as measured in acetonitrile. Both ranges are given because some of the reducible compounds are best measured in water whereas others are best measured in acetonitrile. The desired E$_{178}$ is achieved by appropriate electron withdrawing groups on the CAR$-$ nucleus, or by a combination of a fused ring attached to the nucleus and electron withdrawing groups.

In one embodiment, the reducible compounds can be reduced to provide a detectable species through quinonemethide formation, similar to the description by Van de Sande in *Angew. Chem. Int. Ed. Engl.* 22, pp. 191–209 (1983) and U.S. Pat. No. 4,232,107 (issued Nov. 4, 1980 to Janssens), but which have the desired E$_{\frac{1}{2}}$ properties.

In another embodiment, useful reducible compounds include sulfilimides and sulfonylsulfonamides similar to those described on page 206 of the Van de Sande reference noted above, but which have the desired E$_{\frac{1}{2}}$ properties.

In a preferred embodiment, the reducible compounds of this invention are RIND compounds, i.e. reducible compounds capable of undergoing intramolecular nucleophilic displacement at physiological pH to release one or more shiftable detectable species when a nucleophilic group is generated by at least a one electron reduction of the compound. Such compounds are described in detail in U.S. Ser. No. 824,766, noted above.

Particularly useful RIND compounds are those of a novel class of reducible compounds which have the structure CAR$-$R$^1$ wherein CAR$-$ is

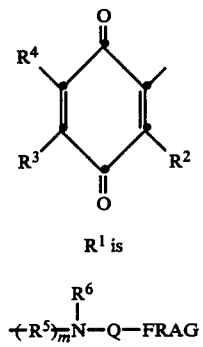

R$^1$ is $$\pmb{+}\text{R}^5\!\pmb{\rightarrow}_{\!m}\!\!\underset{\underset{\text{R}^6}{|}}{\text{N}}\!-\!\text{Q}\!-\!\text{FRAG}$$

wherein m is 0 or 1, and preferably 1. R$^5$ is substituted or unsubstituted alkylene, preferably of 1 or 2 carbon atoms in the backbone (for example, methylene, ethylene or alkoxymethylene). Most preferably, R$^5$ is methylene. Q is carbonyl or thiocarbonyl and preferably carbonyl.

R$^6$ is substituted or unsubstituted alkyl preferably of 1 to 40 carbon atoms (for example, methyl, ethyl, n-propyl, isopropyl, t-butyl, hexyl, decyl, lauryl or benzyl), substituted or unsubstituted cycloalkyl preferably of 4 to 40 carbon atoms (for example, cyclobutyl, cyclohexyl or 4-methylcyclohexyl), substituted or unsubstituted heterocycle preferably of 5 to 40 atoms (carbon and heteroatoms, for example, pyridyl), or substituted or unsubstituted aryl of 6 to 40 carbon atoms (for example, phenyl, xylyl, naphthyl, p-nitrophenyl, anthryl or p-t-butoxyphenyl).

FRAG is a shiftable detectable species as defined above. Preferably, along with the remainder of the molecule, it has a first spectral band(s), but when it is cleaved from the RIND compound, it provides a detectable species having a second spectral band(s), as described above. This species is released in an amount which can be directly related to the amount of reductant present. The specific composition of FRAG can vary considerably depending upon the type of detectable species desired and upon the particular detection means employed.

The shiftable detectable species can be a material which is directly detectable by a suitable means, as well as a material which can react with other substances, for example, analytes, enzymes or other reagents to provide a detectable species. Such species include those detectable by radiometric means, including chromogens (for example, dyes or pigments) which can be detected colorimetrically and fluorogens (for example, fluorescent dyes or probes) which can be detected fluorometrically. Additionally, the detectable species can be a phosphorescent species, a chemiluminescent species, or any other detectable species known to one skilled in the art.

Particularly useful shiftable detectable moieties are chromogens and fluorogens. Examples of useful classes of chromogens are azo, azomethine, nitrophenol, indophenol, indoaniline and triarylmethane dyes, and others known in the art, with azo dyes being preferred. Examples of useful classes of fluorogens are coumarin, umbelliferone, phenalenone and benzphenalenone, fluorescein and rhodamine fluorescent dyes, and others known in the art. Phenalenone dyes are particularly useful.

Useful phosphorescent species include such phosphors as 2′,5′-dibromofluorescein and 4′,5′-diiodofluorescein. A useful chemiluminescent species is luciferin.

FRAG is linked to Q by means of a single bond through a bivalent monoatom linkage which is a part of FRAG. Preferably, the monoatom linkage is oxy, thio or seleno, and most preferably it is oxy. However, when FRAG is a fluorogen, the linkage is oxy or thio.

$R^2$, $R^3$ and $R^4$ in the above quinone structure are independently hydrogen, substituted or unsubstituted alkyl of 1 to 40 carbon atoms (for example, methyl, ethyl, hydroxymethyl, methoxymethyl or benzyl) substituted or unsubstituted aryl (for example, phenyl, naphthyl, methylnaphthyl, p-nitrophenyl, m-methoxyphenyl or phenylsulfonamido) or an electron withdrawing group which generally has a positive Hammett sigma value, and preferably has a sigma value greater than about 0.06. Hammett sigma values are calculated in accordance with standard procedures described, e.g. in *Steric Effects in Organic Chemistry*, John Wiley & Sons, Inc., 1956, pp. 570–574 and *Progress in Physical Organic Chemistry*, Vol. 2, Interscience Publishers, 1964, pp. 333–339. Representative electron withdrawing groups having positive Hammett sigma values include cyano, carboxy, nitro, halo (for example, fluoro, bromo, chloro or iodo), trihalomethyl (for example, trifluoromethyl or trichloromethyl), trialkylammonium, carbonyl, carbamoyl, sulfonyl, sulfamoyl, esters and others known in the art, or alkyl or aryl groups (defined above) substituted with one or more of these electron withdrawing groups. Preferred electron withdrawing groups include p-nitrophenyl, m-nitrophenyl, p-cyanophenyl and 2,5-dichlorophenyl. Aryl groups with methoxy or acetamido groups in the meta position are also useful.

$R^3$ can also be $R^1$ thereby potentially providing a 2:1 molar ratio of detectable species molecules to original RIND compound molecule.

Alternatively, $R^3$ and $R^4$, taken together, can represent the carbon atoms necessary to complete a substituted or unsubstituted fused carbocyclic ring attached to the quinone nucleus. For example, such a ring (mono- or bicyclic) can have from 4 to 8, and preferably from 5 to 7, carbon atoms in the backbone.

Representative preferred RIND compounds of this invention are listed in Table I of U.S. Ser. No. 824,766, noted above.

Other RIND compounds useful in the practice of this invention include those having the appropriate $E_{\frac{1}{2}}$ values and the structure CAR$+R^1)_n$ wherein:

(1) CAR— is a substituted or unsubstituted nucleus of a 1,2-naphthoquinone, 1,2-, 1,4- or 9,10-anthraquinone, 4,4′-diphenoquinone, azuloquinone or 1,6-[10]-anulenoquinone wherein $R^1$ is attached to the nucleus one carbon atom distant or in the peri position from one of the oxo groups of the nucleus. The nucleus can be substituted with one or more electron withdrawing groups as described above for $R^2$ or have one or more fused rings as described above for $R^3$ and $R^4$.

$R^1$ is

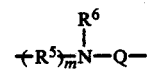

FRAG as defined above, and n is an integer of 1 or 2.

(2) CAR— is

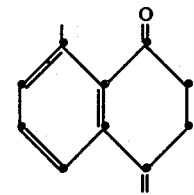

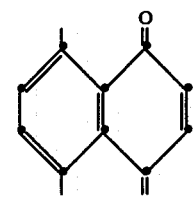

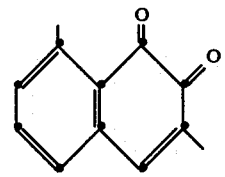

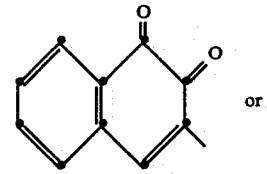

or

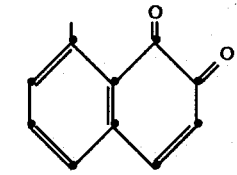

any of which can be substituted with one or more electron withdrawing groups as described above for $R^2$, $R^3$ and $R^4$. $R^1$ is

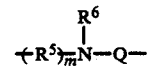

FRAG as defined above, and n is 1 or 2.

(3) CAR— is a substituted or unsubstituted nitrobenzenoid nucleus of the structure

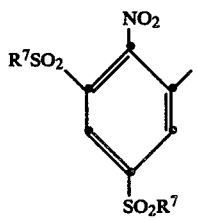

wherein $R^7$ is substituted or unsubstituted alkyl of 1 to 20 carbon atoms (for example, methyl, ethyl, methoxymethyl, isopropyl, dodecyl, hexadecyl or octa decyl), and $R^1$ is

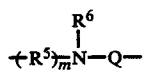

FRAG as defined above and n is 1. These compounds are similar to some described in U.S. Pat. No. 4,139,379 (noted above).

Other useful reducible compounds are described in U.S. Ser. No. 868,479 now U.S. Pat. No. 4,797,357, and U.S. Ser. No. 868,855 entitled WATER-COMPATIBLE REDUCIBLE COMPOUNDS AND THEIR USE IN ANALYTICAL COMPOSITIONS AND METHODS, both filed by Mura et al on May 30, 1986.

All of these reducible compounds can be prepared using techniques and starting materials known in the art or readily apparent to a skilled synthetic chemist.

The oxidizable compounds useful in the practice of this invention are broadly defined as organic compounds which provide a detectable signal in response to oxidation by an electron transfer agent in its oxidized form. Such a signal can be provided by the compound itself or a part thereof which is released in some fashion. Representative oxidizable compounds include substituted and unsubstituted hydroquinones, aminophenols, phenylenediamines and others known to one skilled in the art. These materials are either available commercially or readily prepared using known procedures and starting materials.

In one embodiment, the present invention is practiced with a stoichiometric excess of a reductant which is capable of reducing the oxidized form of the electron transfer agent after its reaction with the reducible compound. Alternatively, in another embodiment, the invention is practiced with a stoichiometric excess of an oxidant which is capable of oxidizing the reduced form of the electron transfer agent after its reaction with the oxidiziable compound. This in the presence of excess reductant or oxidant, the released electron transfer agent is recycled until all of the reducible or oxidizable compound has reacted.

Hence, any compound which will reduce an oxidized electron transfer agent is considered a reductant and can be used in the practice of this invention. A particularly useful reductant is nicotinamide adenine dinucleotide, reduced form (NADH). Nicotinamide adenine dinucleotide phosphate, reduced form (NADPH), flavin adenine dinucleotide, reduced form (FADH), ascorbic acid or salts thereof, cytochromes and ubiquinol are also useful reductants.

Conversely, any compound which will oxidize a reduced electron transfer agent is considered an oxidant and can be used in the practice of this invention. Representative useful oxidants include hydrogen peroxide, ferricyanide, persulfate, ferric chloride and lead dioxide.

Depending upon their water solubilities, the hydrolytic substrates and other components of the compositions of this invention can be either dissolved directly in buffers or in a combination of buffer and water-miscible organic solvents, or solutions can be prepared containing a substrate, buffer, water-miscible organic solvent and surfactant.

When used for the determination of enzymes or organisms, the composition of this invention is buffered at the particular pH required for a given assay. Useful buffers are readily determined by one skilled in the art and include phosphates, borates and organic buffers as reported by Good et al in *Biochem.* 5, 467 (1966) and *Anal. Biochem.* 104, 300 (1980). Surfactants which are useful in the practice of this invention include any surfactants which do not inhibit compound hydrolysis. Generally, for detection of living cells, the useful surfactants are nonionic surfactants.

Useful water-miscible organic solvents include alcohols (for example, methanol, ethanol or propanol), N,N-dimethylformamide, dimethyl sulfoxide, acetonitrile, hexamethylenephosphoramide and the like. The particular solvent to be used for a particular hydrolytic substrate can be readily determined by routine experimentation.

A composition can be prepared in the following general manner with the particular details of such a preparation illustrated in Example 4 below. The hydrolytic substrate is dissolved in the water-miscible solvent at a concentration which depends upon its molecular weight, but generally at from about 0.1 to about 20, and preferably from about 1 to about 10, mg per ml of solvent. In solution assays, the amount of hydrolytic substrate present is at least about 0.01, and preferably from about 10 to about 100, millimolar. A reducible or oxidizable compound can be present in an amount of at least about 0.001, and preferably from about 0.01 to about 1, millimolar. The amount of reductant or oxidant included in the composition or added to it at the time of the assay can be readily determined by a skilled worker in the art, as long as there is stoichiometric excess in relation to the reducible or oxidizable compound respectively.

The determination of living cells, and particularly of bacterial cells, is often carried out in the presence of a nutrient for those cells although its presence is not essential. Any nutrient medium can be used which contains useful carbon, and optionally nitrogen, sources. Suitable nutrient medium having proper components and pH are well known in the art.

Some enzyme analytes require an inducer, that is, a material or a combination of materials that promote the formation of the enzyme in the cell. The type of inducer or induction medium used is dependent upon the enzyme to be formed and determined. In some cases, both an inducer and a nutrient may be needed to promote formation.

The present invention is adaptable to either solution or dry assays. In a solution assay, a composition containing a hydrolytic substrate is contacted by mixing with a liquid test sample containing the living cells or hydrolytic analyte to be determined. Generally the substrate is mixed with the test sample in a suitable container (for example, test tube, petri dish beaker, cuvette or test device). The resulting solution is gently mixed and may be incubated for a relatively short time if desired at a temperature optimum for the particular analyte. The test sample is then evaluated by measuring the resulting detectable species with suitable detection equipment.

The solution assay can also be carried out by contacting a porous absorbent material, for example a paper strip, containing the test sample with a dispersion of the substrate. The analyte in the test sample can migrate from the porous material into the dispersion and initiate the analytical reactions needed for determination.

Alternatively, the method of this invention can be practiced using a dry analytical element. Such an element can be a absorbent carrier material, that is, a thin sheet or strip of self-supporting absorbent or bibulous material, such as filter paper or strips, which contains the hydrolyzable substrate or a dried residue of a composition comprising same. Such elements are known in the art as test strips, diagnostic elements, dip sticks, diagnostic agents and the like.

When employed in dry analytical elements, the substrate can be incorporated into a suitable absorbent carrier material by imbibition or impregnation, or can be coated on a suitable absorbent carrier material. Alternatively, the substrate can be added to the element during an assay. Useful carrier materials are insoluble and maintain their structural integrity when exposed to water or physiological fluids such as urine or serum. Useful carrier materials can be prepared from paper, porous particulate structures, cellulose, porous polymeric films, glass fibers or woven and nonwoven fabrics (synthetic and nonsynthetic). Useful materials and procedures for making such elements are well known in the art as exemplified by U.S. Pat. Nos. 3,092,465 (issued Jun. 4, 1963 to Adams et al), 3,802,842 (issued Apr. 9, 1974 to Lange et al), 3,915,647 (issued Oct. 28, 1975 to Wright), 3,917,453 (issued Nov. 4, 1975 to Milligan et al), 3,936,357 (issued Feb. 3, 1976 to Milligan et al), 4,248,829 (issued Feb. 3, 1981 to Kitajima et al), 4,255,384 (issued Mar. 10, 1981 Kitajima et al), and 4,270,920 (issued Jun. 2, 1981 to Kondo et al), and U.K. Patent 2,052,057 (published Jan. 21, 1981).

A dry assay can be practiced to particular advantage with an analytical element comprising a support having thereon at least one porous spreading zone as the absorbent carrier material. The substrate can be in the spreading zone or in a different zone (for example, a reagent, registration or hydrophilic zone). The spreading zone can be prepared from any suitable fibrous or non-fibrous material or mixtures of either or both.

The spreading zone can be prepared using fibrous materials, either mixed with a suitable binder material or woven into a fabric, as described in U.S. Pat. No. 4,292,272 (issued Sept. 29, 1981 to Kitajima et al) or from polymeric compositions or particulate materials, with or without binding adhesives, as described in U.S. Pat. Nos. 3,992,158 (issued Nov. 16, 1976 to Przybylowicz et al) 4,258,001 (issued Mar. 24, 1981 to Pierce et al) and 4,430,436 (issued Feb. 7, 1984 to Koyama et al) and Japanese Patent Publication 57(1982)-101760 (published Jun. 24, 1982). It is desirable that the spreading zone be isotropically porous, meaning that the porosity is the same in each direction in the zone as created by interconnected spaces or pores.

The dry analytical element of this invention preferably comprises a suitable nonporous support carrying the absorbent carrier material. Such a support can be any suitable dimensionally stable, and preferably, transparent (that is, radiation transmissive) film or sheet material which transmits electromagnetic radiation of a wavelength between about 200 and about 900 nm. A support of choice for a particular element should be compatible with the intended mode of detection (for example, fluorescence, chemiluminescence, reflectance or transmission spectroscopy) and inert to chemical reagents and liquid samples used in the assay. Useful support materials include polystyrene, polyesters, polycarbonates, cellulose esters and others known in the art.

The elements can have more than one zone which are generally in fluid contact with each other, meaning that fluids, reagents and reaction products can pass between superposed regions of adjacent zones. Preferably, the zones are separately coated superposed layers, although two or more zones can be located in a single layer. Besides the patents noted above, suitable element formats and components are described also, for example, in U.S. Pat. Nos. 4,042,335 (issued Aug. 16, 1977 to Clément) and 4,144,306 (noted above) and Reissue 30,267 (reissued May 6, 1980 to Bruschi).

In the elements of this invention, the amount of the hydrolytic substrate can be varied widely, but it is generally present in a coverage of at least about 0.001, and preferably from about 0.05 to about 1, $g/m^2$. The reducible or oxidizable compound can be added to the element during manufacturing or during the assay in a coverage of at least about 0.01, and preferably from about 0.05 to about 0.5, $g/m^2$. Further, the reductant or oxidant can be similarly added to provide a stiochiometric excess in relation to the reducible or oxidizable compound, respectively. Optional, but preferred reagents (for example, nutrient, inducer, buffer, etc.) are generally present in the following coverages:

nutrient: generally at least about 0.05, and preferably from about 0.1 to about 2, $g/m^2$ (used only in living cell detection), buffer: generally at least about 0.1, and preferably from about 0.5 to about 2, $g/m^2$, surfactant: generally at least about 0.1, and preferably from about 0.2 to about 5, $g/m^2$.

inducer: generally at least about $10^{-4}$ $g/m^2$.

One or more of the zones can contain a variety of other desirable, but optional, components, including activators, binders (generally hydrophilic), coupler solvents and the like as is known in the art, as well as any reagents needed for assay of a particular hydrolytic analyte.

A variety of different elements, depending on the method of assay, can be prepared in accordance with the present invention. Elements can be configured in a variety of forms, including elongated tapes of any desired width, sheets, slides or chips.

The assay of this invention can be manual or automated. In general, in using the dry elements, an analyte or living cell determination is made by taking the element from a supply roll, chip packet or other source and physically contacting it with a sample (for example, up to 200 $\mu$l) of the liquid to be tested so that the sample is mixed with the reagents in the element. Such contact can be accomplished in any suitable manner, for example, by dipping or immersing the element into the sample or, preferably, by spotting the element by hand or machine with one or more drops of the sample with a suitable dispensing means. Substantially simultaneously, any other needed reagents, such as reducible compound, reductant, oxidizable compound or oxidant, can be added to the element or test sample if they are not already incorporated in the element. This contact causes the test sample to be mixed within the element with the substrate and other reagents therein.

After sample application, the element is exposed to any conditioning, such as incubation, heating or the like, that may be desirable to quicken or otherwise facilitate obtaining a test result.

Generally, the assay (solution or dry) is carried out under conditions that promote hydrolysis of the hydrolytic substrate by the hydrolytic enzyme. Such hydrolyzing conditions include conditions of pH, ionic strength and temperature which are conducive to hydrolysis. Generally, the pH will vary from one analyte to another, but for most biological analytes will be less than 9, and preferably less than 8. The temperature is not critical but is generally less than about 50° C.

Detection of an analyte or living cell is achieved when the hydrolytic substrate is hydrolyzed releasing an electron transfer agent which reacts with the reducible or oxidizable compound to release a detectable species or a moiety which participates in one or more additional reactions to provide a detectable species. This detectable species can be detected in a suitable manner using appropriate equipment. In a preferred embodiment, the oxidized (or reduced) electron transfer agent is then reduced (oxidized) by the reductant (oxidant) making it available for reaction with additional reducible (or oxidizable) compound. This recycling continues until all of the reducible (or oxidizable) compound is exhausted. Determination can be either a rate determination or an end-point determination.

In the examples which follow illustrating the practice of the invention, the materials used were obtained as follows:

TRITON X-100 surfactant from Rohm and Haas (Philadelphia, Pa.), the bacterial microorganisms from American Type Culture Collection (ATCC in Rockville, Md.), β-galactosidase, esterase (Type II from porcine liver) and β-nicotinamide adenine dinucleotide, reduced form, disodium salt from Sigma Chemical Co. (St. Louis, Mo.), and the remainder were obtained from Eastman Kodak Co. (Rochester, N.Y., U.S.A.) or prepared using known starting materials and procedures.

As used in the context of this disclosure and the claims, I.U. represents the International Unit for enzyme activity defined as one I.U. being the amount of enzyme activity required to catalyze the conversion of 1 micromole of substrate per minute under standard pH and temperature conditions for the enzyme.

EXAMPLE 1

Preparation of Hydrolytic Substrate I

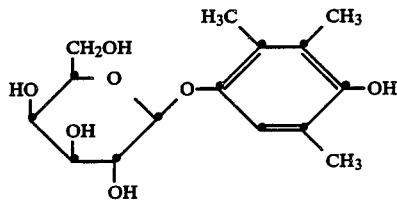

Substrate I

Step 1: Preparation of 4-Hydroxy-2,3,5-trimethylphenyl-2,3,4,6-tetra-O-acetyl-β-D-galactopyranoside A mixture of pentaacetyl-β-D-galactopyranose (Sigma Chemical Co., St. Louis, Mo., 15 g, 38 mmole), 2,3,5-trimethylhydroquinone (Aldrich Chemical Co., Milwaukee, Wis., recrystallized from toluene, 17.5 g, 115 mmole) and freshly distilled phosphorous oxychloride (1.5 g, 9 mmole) were refluxed for 24 hours in 150 ml of toluene in an apparatus to distill off the resulting water and acetic acid. After cooling to room temperature, the reaction mixture was poured into 200 ml of water and the organic phase was separated. The aqueous phase was washed twice with toluene (100 ml), and the organic extracts were combined and dried. The solvent was removed and the residue was purified by column chromatography (silica, 80:20, toluene:ethyl acetate) to give 7.1 g of product. After two recrystallizations from 1:1, methanol:water, the pure β-anomer was obtained, m.p. 160°-161° C. Carbon and hydrogen NMR confirmed the structure.

Step 2: Preparation of Hydrolytic Substrate I

A mixture of 4-hydroxy-2,3,5-trimethylphenyl-2,3,4,6-tetra-O-acetyl-β-D-galactopyranoside (2.9 g, 6 mmole) in 50 ml anhydrous methanol and 6 ml of freshly prepared 1 molar sodium methoxide solution were stirred for 2 hours at 20° C. then, 750 mg of AMBERLYST 15(H+) ion exchange resin (obtained from Aldrich Chemical Co., Milwaukee, Wis.) was added and the mixture stirred for an additional 1.5 hours. The mixture was filtered, the resin was collected and washed with methanol, and the filtrate was concentrated in vacuo to yield 1.9 g of product. The material was recrystallized from 1:1, methanol:water to give pure product, mp 217°-219° C. Mass spectral analysis and carbon and hydrogen NMR confirmed the structure. Calculated for $C_{15}H_{22}O_7$: C, 57.3, H, 7.1, O, 35.6. Found: C, 57.3, H, 6.9, O, 35.2.

EXAMPLE 2

Preparation of Hydrolytic Substrate II

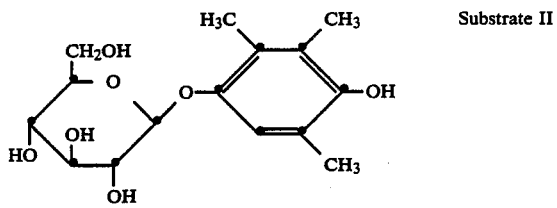

Substrate II

Step 1: Preparation of 4-Hydroxy-2,3,5-trimethylphenyl-2,3,4,6-tetra-O-acetyl-β-D-glucopyranoside A mixture of pentaacetyl-β-D-glucopyranose (Sigma Chemical Co., 15 g, 38 mmole), 2,3,5-trimethylhydroquinone (recrystallized from toluene, 17.5 g, 115 mmole) and freshly distilled phosphorous oxychloride (1.5 g, 9 mmole) were refluxed for 24 hours in 150 ml of toluene in an apparatus to distill off the resulting water and acetic acid. After cooling to room temperature, the reaction mixture was poured into 200 ml of water and the organic layer was separated. The aqueous phase was washed twice with toluene (100 ml), then the organic extracts were combined and dried. The solvent was removed and the residue was purified by column chromatography (silica, 80:20, toluene:ethyl acetate) to yield an oil. After crystallization and recrystallization (4 times) from 1:1, methanol:water, the pure β-anomer was obtained, m.p. 96°-97.5° C. Carbon and hydrogen NMR confirmed the structure.

Step 2: Preparation of Hydrolytic Substrate II

A mixture of 4-hydroxy-2,3,5-trimethylphenyl-2,3,4,6-tetra-O-acetyl-β-D-glucopyranoside (1.53 g, 3.2 mmole) in 50 ml anhydrous methanol and 3.2 ml of freshly prepared 1 molar sodium methoxide solution were stirred for 1.5 hours at 20° C. Then, 500 mg of AMBERLYST 15(H+) ion exchange resin was added and the mixture was stirred for an additional 1.5 hours. The mixture was filtered, the resin was collected and washed with methanol and the filtrate was concentrated in vacuo to yield the product. This material was recrystallized from 50 ml 1:1 methanol:water to yield 500 mg white needles, m.p. 222°-223° C. Mass spectral analysis and carbon and hydrogen NMR confirmed the structure.

EXAMPLE 3

Preparation of Hydrolytic Substrate III

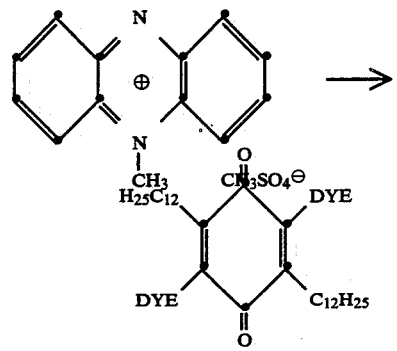

Substrate III wherein DYE is

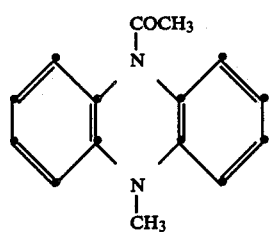

A solution of 10 g of phenazine methosulfate (Aldrich Chemical Co., Milwaukee, Wis.) in 20 ml of acetic anhydride and 20 ml of glacial acetic acid was shaken with 10% palladium/carbon catalyst under hydrogen in a hydrogenation apparatus for 1.5 hours at 25° C. The shaking was stopped and the mixture was allowed to stand at 25° C. for 18 hours. The catalyst was removed by filtration and the filtrate was poured into 1 liter of ice and water, then 5 g of sodium bicarbonate was added and the mixture was stirred for one hour. The precipitated solid was collected by filtration and washed thoroughly with water. After air drying the product weighed 2.14 g, m.p. 139°-141° C. The material was purified by chromatography on silica (the sample was dissolved in methylene chloride and eluted with methylene chloride and 10% diethyl ether) and recrystallization from diethyl ether/ligroin to give pure product, 1.57 g, m.p. 141°-142° C. IR and NMR confirmed the structure.

EXAMPLE 4

Hydrolytic Substrate and Composition for Detecting β-Galactosidase

An analytical composition of this invention was prepared containing 20 ml of hydrolytic substrate I, 10 mmolar in methanol, wherein the electron transfer agent released is 2,3,5-trimethylhydroquinone, 1.5 ml of a dispersion of reducible compound I (prepared by dissolving 14.6 mg of reducible compound I in 500 ml of N,N-dimethylformamide, adding 1 ml of TRITON X-100 and then adding the resulting solution to 50 ml 0.1 molar potassium phosphate buffer, pH 7.5), 30 μl NADH, 10 mmolar in water, 10 ml of diaphorase, 1 mg/ml of water containing 2% bovine serum albumin; and 30 ml of magnesium chloride (0.1 molar in water). The pH of the composition was adjusted to 7.5 with 1.44 ml of 0.1 molar potassium phosphate buffer. Reducible compound I has the structure:

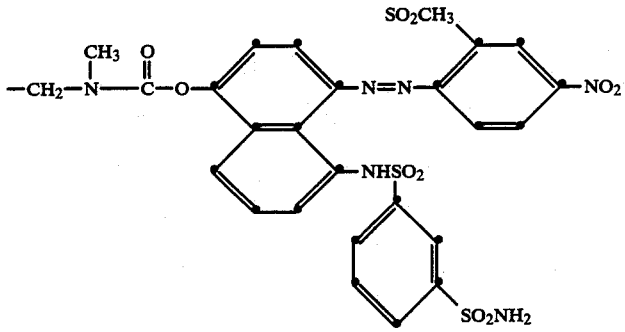

This composition was used to detect two different concentrations of β-galactosidase (from *Escherichia coli*, grade VI, Sigma Chemical Co., St. Louis, Mo.) by measuring the amount of detectable dye released from the reducible compound. The dye density was measured at 635 nm at 37° C. after 30 minutes.

The same analyte was also detected using a standard colorimetric assay as a Control. In this assay, o-nitrophenyl-β-D-galactopyranoside ($2.3 \times 10^{-3}$ molar, identified below as ONPG) was used as the substrate. The reaction also contained magnesium chloride ($10^{-3}$ molar) and potassium phosphate buffer (0.1 molar, pH 7.5). The released dye density was measured at 410 nm at 37° C. after 30 minutes. Table I shows the improvement (increased absorbance) using a composition of this invention. The "Test Absorbance" data are after subtracting background.

TABLE I

| Analyte Concentration | Absorbance (20 Minutes) | |
|---|---|---|
| (I.U./l) | Control | Test |
| 3.6 | 0.85 | 1.20 |

TABLE I-continued

| Analyte Concentration (I.U./l) | Absorbance (20 Minutes) | |
|---|---|---|
| | Control | Test |
| 7.2 | 1.7 | 1.85 |

EXAMPLE 5
Hydrolytic Substrate and Composition for Detecting β-Glucosidase

An analytical composition was prepared containing 100 μl of hydrolytic substrate II (10 mmolar) in 0.1 molar sodium phosphate buffer, 1.5 ml of a dispersion of reducible compound II (prepared as described in Example 4), NADH (30 μl of 10 mmolar in water), 10 μl of diaphorase (1 mg/ml of water) containing 2% bovine serum albumin, and 0.1 molar sodium phosphate buffer (1.3 ml, pH 6.5). Reducible Compound II has the structure:

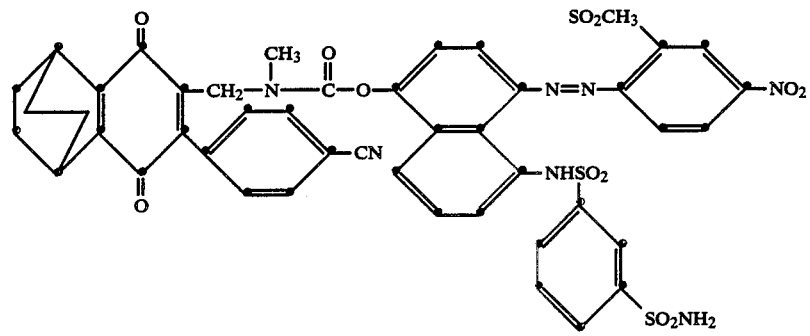

This composition was used to detect the presence of various amounts of the hydrolytic substrate β-glucosidase by measuring the dye released at 635 nm as described in Example 4 above. Table II below lists the analyte concentrations and the resulting dye released after 30 minutes reaction time (identified as change in optical density, ΔOD) at 37° C.

TABLE II

| β-Glucosidase Concentration (I.U./ml) | ΔOD (at 635 nm) |
|---|---|
| 0 | 0.035 |
| 33 | 0.365 |
| 66 | 0.418 |
| 90 | 0.454 |

EXAMPLE 6
Comparative Example Using Hydrolytic Substrate and Composition for the Detection of Esterase This example compares the present invention to a standard assay for porcine liver esterase.

An analytical composition of this invention was prepared containing hydrolytic substrate III (100 μl of 3 mg/ml methanolic solution), 1.5 ml of a dispersion of a reducible compound II (4 mg of reducible compound, 500 μl of TRITON X-100 nonionic surfactant, 25 μl of 0.05 molar phosphate buffer, pH 7.5, and 250 μl of acidified N,N-dimethylformamide), 1.4 ml of additional phosphate buffer and 24 μl NADH (4 mg/ml aqueous solution).

The composition was mixed in a cuvette with 10 μl of esterase solution as indicated in Table III below, and the released dye was measured at 635 nm using a standard spectrophotometer at 28° C. at two-minute intervals.

A titrimetric Control assay was carried out using ethyl butyrate as the substrate by the procedure described by Stotz in *Methods in Enzymology*, Vol. I, p. 657 based on a method of Harrier et al, *J. Biol. Chem.*, 138, p. 111 (1941). Sodium hydroxide (0.1 normal) was used as the titrating solution and bromothymol blue was used as the indicator. Table III also shows the results of this Control assay. It is apparent that the method of the present invention exhibited at least a 100-fold increase in detection over the Control method.

TABLE III

| Enzyme Concentration | Control Assay | Example 3 (ΔOD at 635 nm after 30 Min.) |
|---|---|---|
| Stock* | 0.645 | 3.02 |
| 1:10 dilution | 0.22 | 1.76 |
| 1:100 dilution | 0 | 0.403 |
| 1:1000 dilution | NA | 0.177 |
| 0 | 0 | 0.166 |

*Stock solution made by adding 10 μl of esterase to 1 ml distilled water.
NA = not available.

EXAMPLE 7
Hydrolytic Substrate and Composition for Detecting Acylase Enzyme

In this example a composition of this invention is used to detect an acylase enzyme.

An analytical composition was prepared containing a dispersion of reducible compound II (1.5 ml, prepared as described in Example 6), hydrolytic substrate III (100 μl of 3 mg/ml of methanolic solution), 0.05 molar potassium phosphate buffer, pH 7.5 (1.3 ml), NADH (25 μl of 4 mg/ml buffer solution), and enzyme (100 μl of 10 mg/ml buffer solution of Acylase I, Grade I from porcine kidney, Sigma Chemical Co.). A control solution contained all reagents except enzyme.

Absorbances were read at 635 nm at 37° C., and the change in absorbance (ΔA) was determined after 30 minutes.

| Solution | ΔA, 635 nm, 30 Minutes, 37° C. |
|---|---|
| Control (No Enzyme) | 0.182 |
| Control (No Substrate) | 0.091 |
| Test | 2.208 |

EXAMPLE 8

Hydrolytic Substrate and Composition for Detecting Acylase Enzyme

This example illustrates a substrate and composition of this invention using ascorbate as the reductant to detect an acylase enzyme.

The following solutions were placed in two cuvettes:

Cuvette 1: 1.3 ml of 0.1 molar 2-(4-morpholino)ethanesulfonic acid buffer, 25 ml of acylase I, from porcine kidney, (Sigma Chemical Co.), and 200 μl of hydrolytic substrate III (3 mg/ml methanol solution).

Cuvette 2: 1.3 ml of 2-(4-morpholino)ethanesulfonic acid buffer and 200 μl of hydrolytic substrate III.

Each cuvette was incubated at 37° C. for 15 minutes. Then 1.5 ml of a dispersion of reducible compound II at pH 6.5, prepared as described in Example 6, and 25 μl of 4 mg/ml distilled water solution of sodium ascorbate were added to each cuvette. Absorbances were read at 635 nm and the change in absorbance (ΔA) after 30 minutes was determined.

| Solution | ΔA, 635 nm, 30 Minutes, 37° C. |
|---|---|
| Background Control (Cuvette 2) | 0.250 |
| Example Test (Cuvette 1) | 1.223 |

The invention has been described in detail with particular reference to preferred embodiments thereof, but it will be understood that variations and modifications can be effected within the spirit and scope of the invention.

We claim:

1. A compound containing a non-functioning electron transfer agent which can be enzymatically hydrolyzed to release a functioning electron transfer agent, said compound represented by the formula:

BLOCK-ETA wherein BLOCK is an enzymatically hydrolyzable group selected from the group consisting of:
—CO—R* wherein R* is unsubstituted alkyl, alkenyl, aryl, cycloalkyl or a heterocyclic group,
thioxophosphono or a salt thereof,
a monovalent moiety derived by removal of a hydroxy group from a carboxy group of an amino acid or peptide,
or a mono-, oligo- or polysaccharide linked in a glycosidic bond to ETA,
and ETA is said non-functioning electron transfer agent that when released provides a functioning electron transfer agent selected from the group consisting of phenazine, naphthazine, phenothiazine, a phenazonium compound or a p-benzo- or naphthoquinone electron transfer agent in its reduced form, said BLOCK and ETA being connected through an oxy in the 1- or 4- ring positions where said functioning electron transfer agent is a p-benzo- or naphthoquinone, and an imino linking group from a ring nitrogen where said functioning electron transfer agent is a phenazine, naphthazine, phenothiazine or phenazonium compound,
provided that when BLOCK is thioxophosphono or a salt thereof, or a mono-, oligo- or polysaccharide, ETA provides a p-benzoquinone or naphthoquinone electron transfer agent in its reduced form, said p-benzo- or naphthoquinone having the structure:

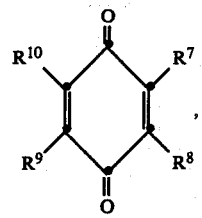

wherein $R^7$ and $R^8$ are independently hydrogen, hydroxy, halo, cyano, nitro, carboxy, carboxyalkyl, carboxamido, sulfonamido, trihaloalkyl, sulfonyl, carboxaldehyde, carbonylalkyl, alkyl, alkenyl, alkoxy, hydroxyalkyl, hydroxyalkoxy, alkoxyalkyl, alkoxyalkoxy, acetoxyalkyl, acetoxyalkoxy, aryl, alkaryl, heterocycle or heteroalkyl, $R^9$ and $R^{10}$ are independently selected from the groups defined for $R^7$ and $R^8$, or taken together supply the atoms needed to complete a 4- to 8- membered fused carbocyclic or heterocyclic ring, provided at least one of $R^7$, $R^8$, $R^9$ and $R^{10}$ is not hydrogen.

2. The compound of claim 1 wherein ETA provides phenazine methosulfate, phenazine ethosulfate, or a benzo- or naphthoquinone as defined.

3. An analytical composition comprising: (a) a reducible compound which is an organic compound which provides a detectable signal in response to reduction by an electron transfer agent in its reduced form, and (b) a compound containing a non-functioning ETA which can be enzymatically hydrolyzed to release a functioning ETA, said compound represented by the formula:

BLOCK-ETA wherein BLOCK is an enzymatically hydrolyzable group selected from the group consisting of:
—CO—R* wherein R* is unsubstituted alkyl, alkenyl, aryl, cycloalkyl or a heterocyclic group.
phosphono or thioxophosphono or a salt thereof,
a monovalent moiety derived by removal of a hydroxy group from a carboxy group of an amino acid or peptide,
or a mono-, oligo- or polysaccharide linked in a glycosidic bond to ETA,
and ETA is said non-functioning electron transfer agent that when released provides a functioning electron transfer agent selected from the group consisting of phenazine, naphthazine, phenothiazine, phenazonium compound or an o- or p- benzo- or naphthoquinone electron transfer agent in its reduced form which is capable of reducing said reducible compound, said BLOCK and ETA being connected through an oxy in the 1-, 2- or 4- ring positions where said functioning electron transfer agent is an o- or p-benzo- or naphthoquinone, and an imino linking group from a ring nitrogen where said functioning electron transfer agent is a phenazine, naphthazine, phenothiazine or phenazonium compound,
provided that when BLOCK is phosphono or thioxophosphono or a salt thereof, or a mono-, oligo- or polysaccharide, ETA provides a p-benzoquinone or naphthoquinone electron transfer agent in its reduced form.

said p-benzo- or naphthoquinone having the structure:

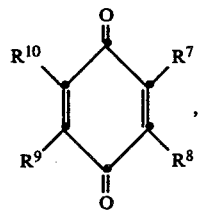

wherein $R^7$ and $R^8$ are independently hydrogen, hydroxy, halo, cyano, nitro, carboxy, carboxyalkyl, carboxamido, sulfonamido, trihaloalkyl, sulfonyl, carboxaldehyde, carbonylalkyl, alkyl, alkenyl, alkoxy, hydroxyalkyl, hydroxyalkoxy, alkoxyalkyl, alkoxyalkoxy, acetoxyalkyl, acetoxyalkoxy, aryl, alkaryl, heteroxycle or heteroalkyl, $R^9$ and $R^{10}$ are independently selected from the groups defined for $R^7$ and $R^8$, or taken together supply the atoms needed to complete a 4- to 8-membered fused carbocyclic or heterocyclic ring, provided at least one of $R^7$, $R^8$, $R^9$ and $R^{10}$ is not hydrogen.

4. The composition of claim 3 wherein said reducible compound has the structure CAR—$R^1$ wherein CAR— is

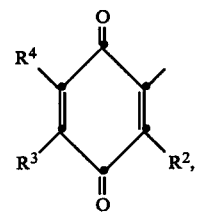

$R^1$ is

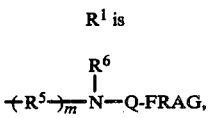

$R^2$ and $R^4$ are independently hydrogen, alkyl, carbocyclic aryl or an electron withdrawing group, $R^3$ is $R^1$, hydrogen alkyl, carbocyclic aryl or an electron withdrawing group, provided that at least one of $R^2$, $R^3$ and $R^4$ is an electron withdrawing group, or $R^3$ and $R^4$, taken together, represent the atoms necessary to complete a strained fused carbocyclic ring, $R^5$ is alkylene of 1 to 2 carbon atoms, $R^6$ is alkyl, cycloalkyl, pyridyl or carbocyclic aryl, Q is carbonyl or thiocarbonyl, FRAG is a detectable moiety which provides a detectable species when released from said reducible compound upon reduction by said functional electron transfer agent, and m is 0 to 1.

5. The composition of claim 3 further comprising a stoichiometric excess of a reductant capable of reducing said electron transfer agent in its oxidized form, but which reductant is not capable of appreciable reaction with said reducible compound.

6. A dry analytical element for the determination of a hydrolytic enzyme or living cells containing same comprising an absorbent carrier material, and containing a compound containing a non-functioning ETA which can be enzymatically hydrolyzed to release a functioning ETA, said compound represented by the formula:

BLOCK-ETA wherein BLOCK is an enzymatically hydrolyzable group selected from the group consisting of:
—CO—R* wherein R* is alkyl, alkenyl, aryl, cycloalkyl or a heterocyclic group, phosphono or thioxophosphono or a salt thereof,
a monovalent moiety derived by removal of a hydroxy group from a carboxy group of an amino acid or peptide,
or a mono-, oligo- or polysaccharide linked in a glycosidic bond to ETA,
and ETA is said non-functioning electron transfer agent that when released provides a functioning electron transfer agent selected from the group consisting of phenazine, naphthazine, phenothiazine, phenazonium compound or an o- or p-benzo- or naphthoquinone electron transfer agent in its reduced form, said BLOCK and ETA being connected through an oxy in the 1-, 2- or 4- ring positions where said functioning electron transfer agent is an o- or p-benzo- or naphthoquinone, and an imino linking group from a ring nitrogen where said functioning electron transfer agent is a phenazine, naphthazine, phenothiazine or phenazonium compound,
provided than when BLOCK is phosphono or thioxophosphono or a salt thereof, or a mono- oligo- or polysaccharide, ETA provides a p-benzoquinone or naphthoquinone electron transfer agent in its reduced form, said p-benzo- or naphthoquinone having the structure:

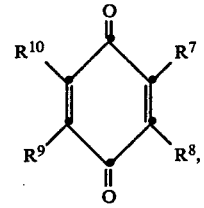

wherein $R^7$ and $R^8$ are independently hydrogen, hydroxy, halo, cyano, nitro, carboxy, carboxyalkyl, carboxamido, sulfonamido, trihaloalkyl, sulfonyl, carboxaldehyde, carbonylalkyl, alkyl, alkenyl, alkoxy, hydroxyalkyl, hydroxyalkoxy, alkoxyalkyl, alkoxyalkoxy, acetoxyalkyl, acetoxyalkoxy, aryl, alkaryl, heterocycle or heteroalkyl, $R^9$ and $R^{10}$ are independently selected from the groups defined for $R^7$ and $R^8$, or taken together supply the atoms needed to complete as 4- to 8-membered fused carbocyclic or heterocyclic ring, provided at least one of $R^7$, $R^8$, $R^9$ and $R^{10}$ is not hydrogen.

7. The element of claim 6 wherein ETA provides phenazine methosulfate, phenazine ethosulfate, or a benzo- or naphthoquinone as defined.

8. The element of claim 6 further comprising a reducible compound which is an organic compound which provides a detectable signal in response to reduction by an electron transfer agent in its reduced form, and a stoichiometric excess of a reductant which is capable of reducing said electron transfer agent in its oxidized form, but which reductant is not capable of appreciable reaction with said reducible compound.

9. The element of claim 8 wherein said reducible compound has the structure CAR—$R^1$ wherein CAR— is

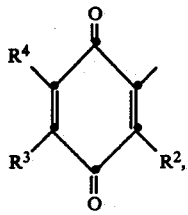

$R^1$ is

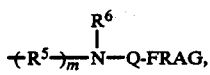

$R^2$ and $R^4$ are independently hydrogen, alkyl, carboxyclic aryl or an electron withdrawing group,
$R^3$ is $R^1$, hydrogen alkyl, carbocyclic aryl or an electron withdrawing group,
provided that at least one of $R^2$, $R^3$ and $R^4$ is an electron withdrawing group, or $R^3$ and $R^4$, taken together, represent the atoms necessary to complete a strained fused carbocyclic ring,
$R^5$ is alkylene of 1 to 2 carbon atoms,
$R^6$ is alkyl, cycloalkyl, pyridyl or carbocyclic aryl,
Q is carbonyl or thiocarbonyl,
FRAG is a detectable moiety which provides a detectable species when released from said reducible compound upon reduction by said functional electron transfer agent, and
m is 0 or 1.

10. The element of claim 8 wherein said reductant is nicotinamide adenine dinucleotide, reduced form.

11. The element of claim 6 further comprising a support having thereon one or more layers, one of said layers being composed of said absorbent carrier material, and containing said enzymatically hydrolyzable compound in one or more of said layers.

12. A method for the determination of a hydrolytic enzyme or living cells containing same comprising the steps of;
    A. under hydrolyzing conditions, contacting a sample of a liquid suspected of containing a hydrolytic enzyme or an organism containing same with a compound containing a non-functioning ETA which can be enzymatically hydrolyzed to release a functioning ETA, said compound represented by the formula:

BLOCK-ETA wherein BLOCK is an enzymatically hydrolyzable group selected from the group consisting of:
    —CO—R* wherein R* is alkyl, alkenyl, aryl, cycloalkyl or a heterocyclic group, phosphono or thioxophosphono or a salt thereof,
    a monovalent moiety derived by removal of a hydroxy group from a carboxy group of an amino acid or peptide,
    or a mono-, o